United States Patent [19]

Blank et al.

[11] 4,375,562
[45] Mar. 1, 1983

[54] PROCESS FOR THE PREPARATION OF BIS-(AMINO-PHENYL)-DISULPHIDES

[75] Inventors: Heinz U. Blank, Odenthal; Theodor Pfister, Wuppertal; Rolf Pütter, Duesseldorf, all of Fed. Rep. of Germany

[73] Assignee: Bayer Aktiengesellschaft, Leverkusen, Fed. Rep. of Germany

[21] Appl. No.: 238,348

[22] Filed: Feb. 26, 1981

[30] Foreign Application Priority Data

Mar. 14, 1980 [DE] Fed. Rep. of Germany ....... 3009846

[51] Int. Cl.³ .............................................. C07C 93/14
[52] U.S. Cl. ..................................................... 564/430
[58] Field of Search ........................................ 564/430

[56] References Cited

U.S. PATENT DOCUMENTS 1,933,217 10/1933 Lantz ................................... 564/430

FOREIGN PATENT DOCUMENTS 462497 1/1950 Canada ................................ 564/430

Primary Examiner—Robert V. Hines
Attorney, Agent, or Firm—Sprung, Horn, Kramer & Woods

[57] ABSTRACT

Process for the preparation of a bis-(amino-phenyl)-disulphide of the formula

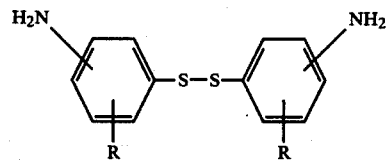

in which
R represents hydrogen or halogen, which comprises contacting an amino-thiophenol of the formula

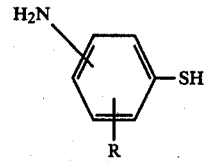

or a salt thereof in which
R has the abovementioned meaning with sulphur or a sulphur-donating substance in an aqueous dispersion at a temperature of 10° to 120° C. and a pH value of 3 to 9.

10 Claims, No Drawings

PROCESS FOR THE PREPARATION OF BIS-(AMINO-PHENYL)-DISULPHIDES

The invention relates to a process for the preparation of bis-(amino-phenyl)-disulphides.

It is known that bis-(amino-phenyl)-disulphides are obtained when 2-nitro- or 4-nitro-chlorobenzene is first reacted with sodium sulphide or sodium sulphide/sulphur in water and then oxidized with atmospheric oxygen or hydrogen peroxide (U.S. Pat. No. 1,933,217; DE-OS (German Offenlegungsschrift No. 2,053,715). Variants of this process which are carried out without the oxidizing agents mentioned have also been disclosed (DE-OS (German Offenlegungsschrift No. 2,503,164; DE-OS (German Offenlegungsschrift No. 2,758,786; U.S. Pat. No. 3,150,186). However, the products obtained in accordance with these methods of preparation contain greater or lesser amounts of impurities, so that for various applications purification processes entailing substantial losses become necessary.

Further, it is known that bis-(2-amino-phenyl)-disulphide is obtained when 2-amino-thiophenol or its sodium salt is reacted with dimethyl sulphoxide or with hydrogen peroxide (U.S. Pat. Nos. 3,981,809; 4,136,118). However, dimethyl sulphoxide and hydrogen peroxide are expensive oxidizing agents compared to atmospheric oxygen and sulphur.

Equally, it is known to use sulphur for the preparation of aliphatic disulphides from mercaptans, the reaction being carried out in the presence of bases, such as alkali metal hydroxides or tertiary aliphatic amines, and in the presence of alcohols as solvents (U.S. Pat. No. 3,340,324), or of N-methylpyrrolidone or isopropanol, optionally mixed with water, as the solvent (U.S. Pat. No. 3,994,979), or in aliphatic disulphides as solvents (German No. 1,214,220).

A process has now been found for the preparation of a bis-(amino-phenyl)-disulphide of the formula

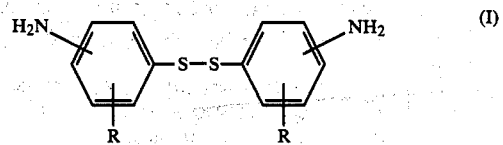

in which
R represents hydrogen or halogen,
which is characterized in that an amino-thiophenol of the formula

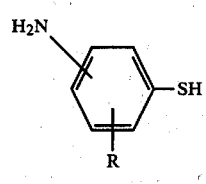

or a salt thereof in which
R has the above-mentioned meaning
is reacted with sulphur or with an inorganic sulphur-donating substance in aqueous dispersion at a temperature of 10° to 120° C. and a pH value of 3 to 9.

As examples of halogen, fluorine, chlorine, bromine and iodine, preferably chlorine or bromine, and especially preferentially chlorine, may be mentioned.

The process according to the invention can be represented by the following equation for the reaction of 2-amino-thiophenol and sulphur:

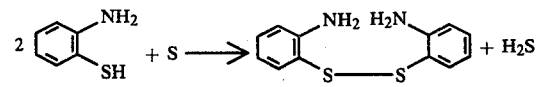

The following may be mentioned as examples of the amino-thiophenol for the process according to the invention: 2-amino-thiophenol, 4-amino-thiophenol, 2-chloro-4-amino-thiophenol, 2-bromo-4-amino-thiophenol, 4-chloro-2-amino-thiophenol, 4-bromo-2-amino-thiophenol, 3-chloro-2-amino-thiophenol, 6-chloro-2-amino-thiophenol and 3-chloro-4-amino-thiophenol.

Preferred amino-thiophenols for the process according to the invention are those in which R represents hydrogen or chlorine.

The use of 2-amino-thiophenol is particularly preferred for the process according to the invention.

If a salt of an amino-thiophenol is used in the inventive process, the following salts may be mentioned: alkali salts as the sodium or potassium salt or alkaline earth salts as the magnesium or calcium salt. Preferably the sodium salt is used as an amino-thiophenol salt.

Amino-thiophenols are known compounds and can be prepared in accordance with known processes, for example by reaction of chloro-nitro-benzenes with bisulphides or sulphides (DE-OS (German Offenlegungsschrift No. 2,127,898).

In the process according to the invention, the amino-thiophenols are reacted with sulphur. For this, the sulphur can be employed in the form of elementary sulphur, such as sulphur powder, sulphur flakes or flowers of sulphur, or via an inorganic sulphur-donating substance. As inorganic sulphur-donating substances there may be mentioned inorganic polysulphides, such as disulphides or trisulphides, and thiosulphates, such as sodium thiosulphate or the thiosulphuric acid liberated on acidification (Gmelins Handbuch der anorganischen Chemie (Gmelins Handbook of Inorganic Chemistry), 8th edition, volume 9, page 874, Verlag Chemie 1960).

Sulphur of the inorganic sulphur-donating substance is employed in the process according to the invention in an amount such that per mol of amino-thiophenol 0.4 to 0.7 mol, preferably 0.5 to 0.55 mol, of sulphur is present.

The process according to the invention is carried out at a temperature of 10° to 120° C., preferably 50° to 110° C. Particularly preferentially, it is carried out at the reflux temperature of the reaction mixture.

The process according to the invention is carried out at a pressure of between 0.01 and 1 bar, preferably 0.5 and 1 bar. Particularly preferentially, it is carried out under normal pressure. The pH-value for carrying out the process according to the invention can lie in the range from 3 to 9, preferably in the range from 4 to 8. When using salt-like sulphur-donating substances, such as sodium thiosulphate, and/or when using the amino-thiophenols in the form of their salts, the pH value is adjusted by addition of a small amount of a mineral acid or of an organic acid. In the reaction of the amino-thiophenols with sulphur, the requisite pH value in general becomes established without further auxiliaries. For the case where an acid is used to adjust the pH, there may be mentioned, for example, a strong mineral acid, such as hydrochloric acid or sulphuric acid, a weak mineral acid, such as, for example, carbonic acid (carbon dioxide in water) or an organic acid, such as acetic acid or formic acid.

To carry out the process according to the invention, the starting components are dispersed in water at room temperature and are then heated, with stirring, to the reaction temperature, in the course of which the hydrogen sulphide formed in the reaction is evolved. The hydrogen sulphide is isolated by conventional methods or is converted, for example by absorption in alkali metal hydroxide solutions and conversion to the corresponding alkali metal salt, or by oxidation to sulphur. Towards the end of the reaction, in order substantially to remove the residual hydrogen sulphide, a slight vacuum is applied to the reaction mixture or a stream of a carrier gas, for example nitrogen or air, is passed through the reaction mixture. After the reaction mixture has cooled, for example to a temperature of between 0° and 20° C., the product can be isolated in the customary manner, for example by filtering, suction-filtering or centrifuging.

Surprisingly, the bis-(amino-phenyl)-disulphides are obtained, according to the process of the invention, in virtually quantitative yields and in high purity, whilst according to the prior art processes products which are more or less heavily contaminated are always obtained. The bis-(amino-phenyl)-disulphides preparable according to the process of the invention can be used as fungicides, components for lubricating oil additives, components for polyurethane prepolymers, rubber peptising agents and intermediates for the synthesis of benzthiazole derivatives (DE-OS (German Offenlegungsschrift) No. 2,503,164).

EXAMPLE 1

25 g (0.2 mol) of 2-amino-thiophenol and 3.5 g (0.11 mol) of sulphur are dispersed in 150 ml of water and the mixture is heated to the boil under reflux, and stirred, for 90 minutes. After cooling to 20° C., the mixture is filtered and the product is dried at 40° C. in a water-pump vacuum. Yield 25 g (100% of the theoretical yield); melting point 93° C. According to a check by thin layer chromatography (methylene chloride on silica gel), the product consists of the single compound bis-(2-amino-phenyl)-disulphide.

EXAMPLE 2

25 g (0.2 mol) of 2-amino-thiophenol and 25 g (0.1 mol) of sodium thiosulphate pentahydrate are initially introduced into 150 ml of water and the mixture is heated under reflux, and stirred, for 2 hours. After cooling to 20° C., the mixture is filtered and the product is dried at 40° C. in a waterpump vacuum.

Yield: 20.5 g (82% of the theoretical yield) of bis-(2-amino-phenyl)-disulphide; melting point 93° C.

EXAMPLE 3

The experiment is carried out as described in Example 2, with the difference that the pH value is adjusted to 5 at about 80° C. by dropwise addition of acetic acid.

Yield: 24.5 g (98% of theory) of bis-(2-amino-phenyl)-disulphide; melting point 93° C.

EXAMPLE 4

The experiment is carried out as described in Example 2, with the difference that carbon dioxide is passed in at about 80° C. and the pH value is adjusted to 5 by dropwise addition of 40% strength sulphuric acid.

Yield: 24.5 g (98% of theory) of bis-(2-amino-phenyl)-disulphide; melting point 93° C.

What is claimed is:

1. Process for the preparation of a bis-(amino-phenyl)-disulphide of the formula

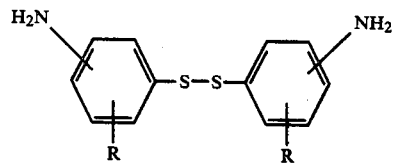

in which

R represents hydrogen or halogen, which consists essentially of contacting an amino-thiophenol of the formula

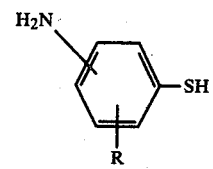

or a salt thereof in which

R has the above-mentioned meaning with sulphur or thiosulphate which donates sulphur in an aqueous dispersion at a temperature of 10° to 120° C. and a pH value of 3 to 9 employing a reaction mixture consisting essentially of said amino thiophenol or salt thereof, water and elemental sulphur or said thiosulphate.

2. Process according to claim 1, wherein said sulphur or thiosulphate is employed in such amount that 0.4 to 0.7 mol of sulphur is available per mol of amino-thiophenol.

3. Process according to claim 1, wherein said sulphur or thiosulphate is employed in an amount of 0.5 to 0.55 mol per mol of amino-thiophenol.

4. Process according to claim 1, wherein the reaction is carried out at 50° to 110° C.

5. Process according to claim 1, wherein the reaction is carried out at the reflux temperature of the reaction mixture.

6. Process according to claim 1, wherein the reaction mixture has a pH value of 4 to 8.

7. Process according to claim 1, wherein the reaction is carried out with elementary sulphur.

8. Process according to claim 1, wherein the reaction is carried out employing sodium thiosulphate.

9. Process according to claim 1, wherein a chlorine-substituted or bromine-substituted amino-thiophenol is reacted.

10. Process according to claim 1, wherein an unsubstituted amino-thiophenol is reacted.

* * * * *

UNITED STATES PATENT AND TRADEMARK OFFICE
CERTIFICATE OF CORRECTION

PATENT NO. : 4,375,562
DATED : March 1, 1983
INVENTOR(S) : Heinz Ulrich Blank et al It is certified that error appears in the above-identified patent and that said Letters Patent is hereby corrected as shown below:

Col. 4, line 65    Insert omitted Claim 12 to be renumbered claim 11

--Process according to claim 1, wherein said thiosulphate is sodium thiosulfate pentahydrate.--

On the title page "10 Claims" should read -- 11 Claims --.

Signed and Sealed this

Nineteenth Day of July 1983

[SEAL]

Attest:

GERALD J. MOSSINGHOFF

Attesting Officer    Commissioner of Patents and Trademarks